United States Patent
Kaditz et al.

(10) Patent No.: US 10,936,180 B2
(45) Date of Patent: Mar. 2, 2021

(54) USER INTERFACE FOR MEDICAL INFORMATION

(71) Applicant: Q Bio, Inc, San Francisco, CA (US)

(72) Inventors: Jeffrey H. Kaditz, Wilson, WY (US); Robert A. Novoa, Miami, FL (US)

(73) Assignee: Q Bio, Inc., San Carlos, CA (US)

( * ) Notice: Subject to any disclaimer, the term of this patent is extended or adjusted under 35 U.S.C. 154(b) by 155 days.

(21) Appl. No.: 15/924,050

(22) Filed: Mar. 16, 2018

(65) Prior Publication Data

US 2018/0267700 A1 Sep. 20, 2018

Related U.S. Application Data

(60) Provisional application No. 62/472,489, filed on Mar. 16, 2017.

(51) Int. Cl.
*G06F 3/0484* (2013.01)
*G16H 40/63* (2018.01)
*G06F 3/0481* (2013.01)
*G16H 50/30* (2018.01)
*G16H 50/20* (2018.01)
*G16Z 99/00* (2019.01)

(52) U.S. Cl.
CPC ...... *G06F 3/04847* (2013.01); *G06F 3/04817* (2013.01); *G06F 3/04845* (2013.01); *G16H 40/63* (2018.01); *G16H 50/20* (2018.01); *G16H 50/30* (2018.01); *G16Z 99/00* (2019.02); *G06F 2203/04806* (2013.01)

(58) Field of Classification Search
CPC .... G06F 3/04847; G16H 50/30; G16H 50/20; G16H 40/63

USPC .......................................................... 715/765
See application file for complete search history.

(56) References Cited

U.S. PATENT DOCUMENTS

| | | |
|---|---|---|
| 4,729,892 A | 3/1988 | Beall |
| 5,486,762 A | 1/1996 | Freedman et al. |
| 5,717,879 A * | 2/1998 | Moran ................ G11B 27/28 |
| | | 715/716 |

(Continued)

FOREIGN PATENT DOCUMENTS

| | | |
|---|---|---|
| EP | 3093677 | 11/2016 |
| WO | WO-2014205275 | 12/2014 |

(Continued)

OTHER PUBLICATIONS

Drescher et al., article titled "Longitudinal Screening Algorithm That Incorporates Change Over Time in CA125 Levels Identifies Ovarian Cancer Earlier Than a Single-Threshold Rule".

(Continued)

*Primary Examiner* — Stephen S Hong
*Assistant Examiner* — Broderick C Anderson
(74) *Attorney, Agent, or Firm* — Aurora Consulting LLC; Steven E. Stupp; Ashley Sloat

(57) ABSTRACT

A user interface for medical information includes a timeline that can be highlighted or selected by a time window with a time duration, and the information plots of biomarkers displayed in subsystem displays can update to display the biomarker information for the time duration highlighted by the time window. The trendline, baseline, and data points shown on the information plot(s) can also be adjusted to display only information during the time duration highlighted or selected by the time window.

20 Claims, 5 Drawing Sheets

(56) References Cited

U.S. PATENT DOCUMENTS

| | | |
|---|---|---|
| 5,793,210 A | 8/1998 | Pla |
| 6,084,408 A | 7/2000 | Chen |
| 6,148,272 A | 11/2000 | Bergstrom |
| 6,392,409 B1 | 5/2002 | Chen |
| 6,678,669 B2 | 1/2004 | Lapointe |
| 7,924,002 B2 | 4/2011 | Lu |
| 7,940,927 B2 | 5/2011 | Futa |
| 7,974,942 B2 | 7/2011 | Pomroy |
| 8,108,311 B2 * | 1/2012 | Herlitz .................. G06Q 10/00 705/51 |
| 8,401,870 B2 * | 3/2013 | Whelchel .............. G06Q 50/24 705/2 |
| 8,432,165 B2 | 4/2013 | Weiger Senften |
| 8,502,532 B2 | 8/2013 | Assmann |
| 8,686,727 B2 | 4/2014 | Reddy |
| 8,723,518 B2 | 5/2014 | Seiberlich |
| 8,736,265 B2 | 5/2014 | Boernert |
| 8,775,213 B2 * | 7/2014 | Hughes ................. G16H 10/60 705/3 |
| 9,513,359 B2 | 12/2016 | Koch |
| 9,514,169 B2 | 12/2016 | Mattsson |
| 10,402,910 B1 * | 9/2019 | Kunz .................... G06Q 40/12 |
| 2002/0155587 A1 | 10/2002 | Opalsky |
| 2002/0177771 A1 | 11/2002 | Guttman |
| 2003/0135087 A1 * | 7/2003 | Hickle ................... G16H 20/10 600/26 |
| 2003/0210043 A1 | 11/2003 | Freedman |
| 2005/0137476 A1 | 6/2005 | Weiland |
| 2005/0181466 A1 | 8/2005 | Dambinova |
| 2008/0065665 A1 | 3/2008 | Pomroy |
| 2008/0081375 A1 | 4/2008 | Tesiram |
| 2008/0082834 A1 | 4/2008 | Mattsson |
| 2008/0189634 A1 * | 8/2008 | Tevanian ............... G06Q 40/06 715/764 |
| 2009/0315561 A1 | 12/2009 | Assmann |
| 2010/0131518 A1 | 5/2010 | Elteto |
| 2010/0142823 A1 | 6/2010 | Wang |
| 2010/0177188 A1 | 7/2010 | Kishima |
| 2010/0189328 A1 | 7/2010 | Boernert |
| 2010/0244827 A1 | 9/2010 | Hennel |
| 2010/0306854 A1 | 12/2010 | Neergaard |
| 2011/0004071 A1 * | 1/2011 | Faiola ................... A61B 5/7445 600/300 |
| 2011/0095759 A1 | 4/2011 | Bhattacharya |
| 2011/0166484 A1 | 7/2011 | Virta |
| 2012/0124161 A1 | 5/2012 | Tidwell |
| 2013/0275718 A1 | 10/2013 | Ueda |
| 2013/0294669 A1 | 11/2013 | El-Baz |
| 2013/0338930 A1 | 12/2013 | Senegas |
| 2014/0019915 A1 * | 1/2014 | Livermore ............ G06F 16/904 715/838 |
| 2014/0062475 A1 | 3/2014 | Koch |
| 2014/0336998 A1 | 11/2014 | Cecchi |
| 2015/0003706 A1 | 1/2015 | Eftestøl |
| 2015/0032421 A1 | 1/2015 | Dean |
| 2015/0040225 A1 | 2/2015 | Coates |
| 2015/0089574 A1 | 3/2015 | Mattsson |
| 2015/0370904 A1 * | 12/2015 | Joshi .................... G06F 16/903 707/722 |
| 2016/0007968 A1 | 1/2016 | Sinkus |
| 2016/0127123 A1 | 5/2016 | Johnson |
| 2017/0011514 A1 | 1/2017 | Westerhoff |
| 2017/0038452 A1 | 2/2017 | Trzasko |

FOREIGN PATENT DOCUMENTS

| | | |
|---|---|---|
| WO | WO-2015183792 | 12/2015 |
| WO | WO-2016073985 | 5/2016 |

OTHER PUBLICATIONS

"I. Kononenko "Machine learning for medical diagnosis: history, state of the art and perspective" Artificial Intelligence in Medicine 23 (2001) 21 pgs , Non-final office action dated Mar. 8, 2018".

"Kwan et al: "MRI Simulation-Based Evaluation of Image-Processing and Classification Mehtods" IEEE Transactions on Medical Imaging. vol. 18 No. 11, Nov. 1999, , Final office action dated Jun. 28, 2018", 13 pgs.

Siemens. Magnetic Resonance Imaging. (Dec. 2012) [retrieved on Jun. 27, 2017, https://w5.siemens.com/web/ua/ru/medecine/detection_diagnosis/magneti_resonans/035-15-MRI-scaners/Documents/mri-magnetom-family_brochure-00289718.pdf] 6 pgs.

International Application Serial No. PCT/US2016/040215, International Search Report dated Sep. 19, 2016, 2 pgs.

International Application Serial No. PCT/US2017/035073, Written Opinion dated Aug. 11, 2017, 6 pgs.

International Application Serial No. PCT/US2016/040578, International Search Report dated Sep. 19, 2016, 2 pgs.

International Application Serial No. PCT/US2016/040215, International Preliminary Report on Patentability and Written Opinion dated Jan. 9, 2018.

Gualda et al. SPIM-fluid: open source light-sheet based platform for high-throughput imaging. Biomed Opt Express (Nov. 1, 2015} vol. 6, No. 11, 10 pgs.

G. Schultz, Magnetic Resonance Imaging with Nonlinear Gradient Fields: Signal Encoding and Image Reconstruction Springer Verlag, New York, 2013), Chapter 2, 10pgs.

International Application Serial No. PCT/US2017/035071, International Search Report dated Aug. 22, 2017, 2 pgs.

International Application Serial No. PCT/US2017/022842, International Search Report dated May 23, 2017, 2 pgs.

International Application Serial No. PCT/US2016/051204, International Search Report dated Nov. 28, 2016, 2 pgs.

International Application Serial No. PCT/US2017/035071, Written Opinion dated Aug. 22, 2017, 7 pgs.

International Application Serial No. PCT/US2016/040215, Written Opinion dated Sep. 19, 2016, 9 pgs.

International Application Serial No. PCT/US2016/051204, Written Opinion dated Nov. 28, 2016, 10 pgs.

International Application Serial No. PCT/US2016/040578, Written Opinion dated Sep. 19, 2016, 9 pgs.

International Application Serial No. PCT/US2017/022911, International Search Report dated Jul. 19, 2017, 4 pgs.

International Application Serial No. PCT/US2017/022911, Written Opinion dated Jul. 19, 2017, 10 pgs.

International Application Serial No. PCT/US2017/035073, International Search Report dated Aug. 11, 2017, 2 pgs.

International Application Serial No. PCT/US2017/022842, Written Opinion dated May 23, 2017, 4 pgs.

Hasenkam et al., "Prosthetic Heart Valve Evaluation by Magnetic Resonance Imaging," European Journal of Cardio-thoracic Surgery 16 (1999) 300-305.

Nestares et al., "Robust Multiresolution Alignment of MRI Brain Volumes," Magnetic Resonance in Medicine 43:705-715 (2000).

* cited by examiner

USER INTERFACE FOR MEDICAL INFORMATION

CROSS-REFERENCE TO RELATED APPLICATIONS

This application claims the benefit of U.S. Provisional Patent Ser. No. 62/472,489, entitled "User Interface for Medical Information," filed Mar. 16, 2017, the entirety of which is herein incorporated by reference.

TECHNICAL FIELD

The described embodiments relate generally to medical information systems, and more specifically to a user interface for medical information that can display information about a medical subject over time and display the information in a way that is useful for medical practitioners and medical subjects to improve their understanding, diagnosis and treatments, and ultimately outcomes.

SUMMARY

Trends in connectivity and in medical imaging technology are resulting in dramatic changes in people's lives. For example, the Internet now allows doctors, researchers, and data scientists to access vast amounts of anonymized information, as well as the ability to interact with individual patients and provide diagnoses around the world. This remote electronic capability has improved the quality of healthcare and reduced costs. Similarly, the increasingly powerful computing and communication capabilities of cloud computing and infrastructure as a service (IAAS) product offerings from companies such as Amazon Web Services and Cloudera combined with portable electronic devices (such as smartphones and tablets), as well as a large and growing set of applications, are accelerating these improvements, and the ability to leverage medical information to perform a wide variety of diagnoses.

The system is displaying medical information over a timeline, and the method of sorting and displaying this medical information can be applied to better detect anomalies on an individual basis; what is normal in one body might be slightly different than what is normal in another body, and clusters of medical samples reflecting various shades of normal can help classify what is normal for an individual and/or a group by using both symptomatic and asymptomatic samples, benign and non-benign tissue samples, quantitative measurements such as tensor field maps (TFM), Magnetic Resonance (MR) spectra, or other measurements. Finally, the amount of data that can be captured about each patient and even each sample over time is much larger than the amount of data that can be processed by a single medical practitioner, so any improvement to the visualization that allows a medical practitioner improves their ability to use as much information as possible when reviewing a patients records, and possibly improve the diagnosis accuracy and treatment outcome, as well as monitoring responses to treatments.

This document outlines a system to display medical information about a life form and fluid and tissue samples and measurement information about those samples. Another unique aspect of this system is that it is optimized to highlight both symptomatic and asymptomatic biological subsystems, as it is just as important to recognize healthy tissue, as it is to recognize pathology. It is also comforting to patients and medical subjects to know that their measurements are in line with their own normal healthy benchmarks.

One aspect of the present disclosure is directed to a computer-implemented method for displaying and analyzing medical information. In some embodiments, the method includes: generating a timeline configured to display a plurality of icons comprising one or more of: a life form icon, a biological sample icon, a measurement icon, a sample indicator icon, a treatment indicator icon, and combinations thereof; generating a sliding window on the timeline, such that the sliding window highlights a subset of the plurality of icons and has an adjustable width and location; and displaying data points in information plots in a subsystem display, such that the data points are related to the subset of the plurality of icons highlighted in the sliding window.

In some embodiments, the sample indicator is a representation of a quantity of the data points collected at a specific point in time.

In some embodiments, the data points are biomarkers. In some embodiments, the method further includes ordering the data points based on one or more of: relevance, a degree of change relative to a previous data point, relatedness to other data points, a label, relative volatility, relative stability, health risk, deviations from expected values, increases in a rate of change of a data point, medical practitioner input, and combinations thereof.

In some embodiments, the method further includes receiving a user input to adjust one or more of a width and a location of the sliding window. In some embodiments, the method further includes receiving a user input to zoom in on a subset of the plurality of icons. In some embodiments, adjusting the sliding window captures one of: a same duration time window, a different duration time window, a different start time, a different end time, and combinations thereof. In some embodiments, the method further includes updating the data points displayed in the subsystem display when the sliding window is adjusted.

In some embodiments, the method further includes displaying one or more of the biological sample icon, the measurement icon, the sample indicator icon, and the treatment indicator icon on the life form icon to represent an approximate location of one or more of: a sample, a biological sample, a measurement, a treatment, and combinations thereof.

In some embodiments, the data points include one or more data points from outside the sliding window for interpolation.

In some embodiments, the method further includes decrypting the data points.

In some embodiments, the subsystem display includes one or both of a baseline and a trend line.

In some embodiments, the biological sample icon represents one or more of: a blood sample, a urine sample, a saliva sample, a hair sample, a nail sample, a skin sample, a bone fragment sample, a biopsy, a microbiome sample, a stool sample, and combinations thereof.

In some embodiments, the measurement icon represents one or more of: MR techniques, X-ray techniques, imaging techniques, vital signs, genetic information, sample analyses, and combinations thereof.

In some embodiments, the method further includes: receiving search criteria from a user; and automatically adjusting the sliding window based on the search criteria.

Another aspect of the present disclosure is a computer-program product including a non-transitory computer-readable storage medium and a computer-program embedded therein configured to display and analyze medical information. In some embodiments, the computer-program includes: instructions for generating a timeline configured to display a plurality of icons comprising one or more of: a life form icon, a biological sample icon, a measurement icon, a sample indicator icon, a treatment indicator icon, and combinations thereof; instructions for generating a sliding window on the timeline, such that the sliding window highlights a subset of the plurality of icons and has an adjustable width and location; and instructions for displaying data points in information plots in a subsystem display, such that the data points are related to the subset of the plurality of icons highlighted in the sliding window.

In some embodiments, the computer-program mechanism includes instructions for transforming the data points, such that transforming includes one or more of: filtering, adding moving averages, applying filtering techniques, applying volatility measurements, applying estimates, applying predictions, applying interpolations, applying visualizations, and combinations thereof.

Another aspect of the present disclosure is a system for displaying and analyzing medical information. In some embodiments, the system includes: a processor subsystem configured to execute a program module; and a memory subsystem, coupled to the processor subsystem, configured to store the program module. In some embodiments, the program module includes instructions for: generating a timeline configured to display a plurality of icons comprising one or more of: a life form icon, a biological sample icon, a measurement icon, a sample indicator icon, a treatment indicator icon, and combinations thereof; generating a sliding window on the timeline, such that the sliding window highlights a subset of the plurality of icons and has an adjustable width and location; and displaying data points in information plots in a subsystem display, such that the data points are related to the subset of the plurality of icons highlighted in the sliding window.

In some embodiments, the program module further includes instructions for receiving user input via an input capture interface, such that the user input includes one or more of: search criteria for automatically adjusting the sliding window, an adjustment of a width of the sliding window, an adjustment of a location of the sliding window, and combinations thereof.

In some embodiments, the program module further includes instructions for communicating the user input from the input capture device through an interface circuit to the processing subsystem.

In some embodiments, the system further includes a display coupled to the processing subsystem and configured to display the timeline.

The preceding summary is provided as an overview of some exemplary embodiments and to provide a basic understanding of aspects of the subject matter described herein. Accordingly, the above-described features are merely examples and should not be construed as narrowing the scope or spirit of the subject matter described herein in any way. Other features, aspects, and advantages of the subject matter described herein will become apparent from the following Detailed Description, Figures, and Claims.

BRIEF DESCRIPTION OF THE FIGURES

The foregoing is a summary, and thus, necessarily limited in detail. The above-mentioned aspects, as well as other aspects, features, and advantages of the present technology are described below in connection with various embodiments, with reference made to the accompanying drawings.

The illustrated embodiments are merely examples and are not intended to limit the disclosure. The schematics are drawn to illustrate features and concepts and are not necessarily drawn to scale.

DETAILED DESCRIPTION

The foregoing is a summary, and thus, necessarily limited in detail. The above-mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the contemplated invention(s). Other embodiments may be utilized, and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

The system is displaying medical information over a timeline, and the method of sorting and displaying this medical information can be applied to better detect anomalies on an individual basis; what is normal in one body might be slightly different than what is normal in another body, and clusters of medical samples reflecting various shades of normal can help classify what is normal for an individual and/or a group by using both symptomatic and asymptomatic samples, benign and non-benign tissue samples, quantitative measurements such as tensor field maps (TFM), Magnetic Resonance (MR) spectra, or other measurements. Finally, the amount of data that can be captured about each patient and even each sample over time is much larger than the amount of data that can be processed by a single medical practitioner. Any improvement to the visualization is needed that allows a medical practitioner to improve his ability to use as much information as possible when reviewing a patients' records, and possibly improve the diagnosis accuracy and treatment outcome, as well as monitoring responses to treatments.

Figure 1:
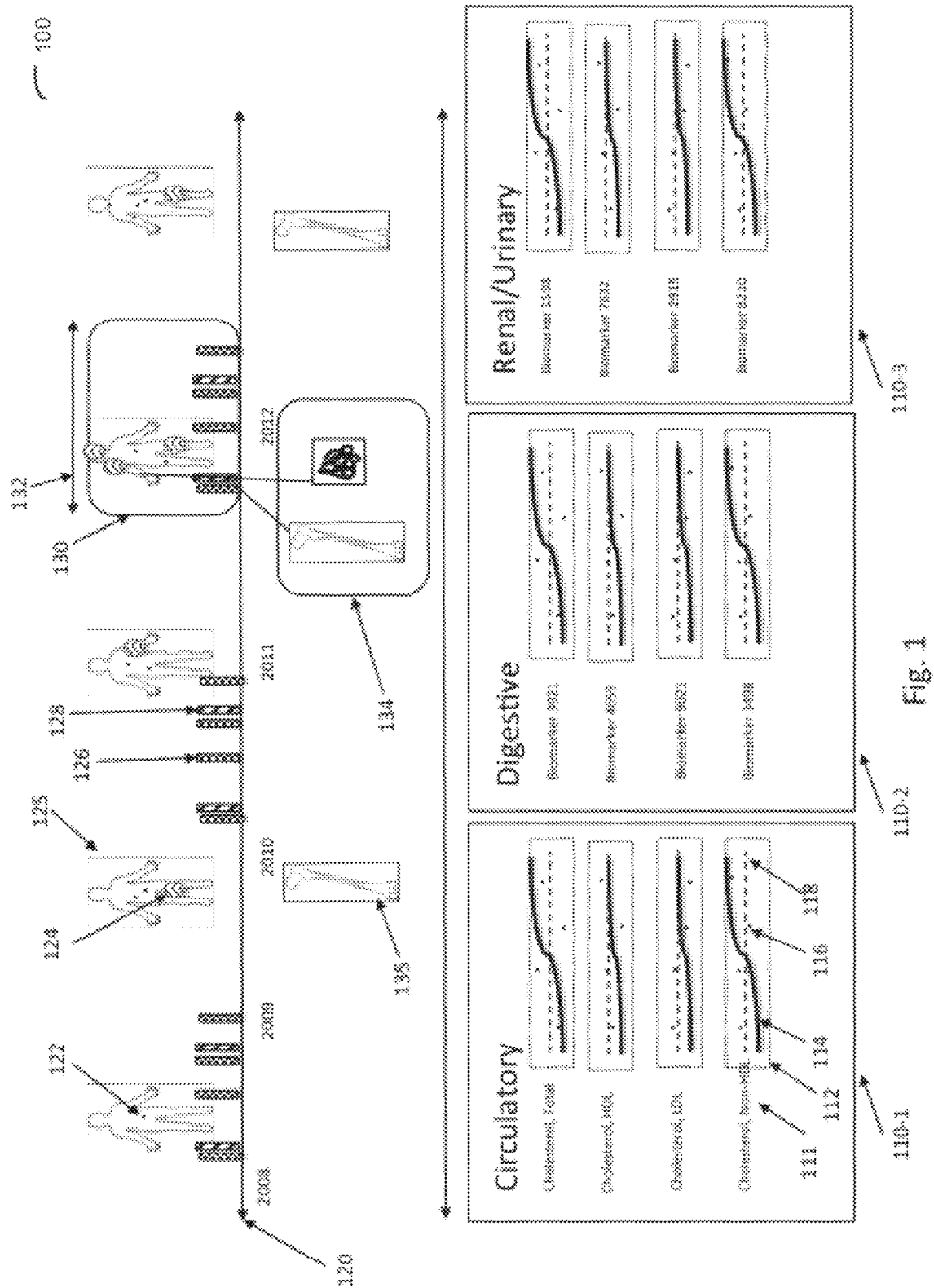
FIG. 1 is a block diagram illustrating a user interface for medical information.

As shown in FIG. 1, a user interface for medical information 100 includes a timeline 120, which can display icons for a human 125 or other life form, icons for biological samples 122, icons for measurements 124, icons for sample indicators 126, icons for treatment indicators 128, as well as subsystem displays 110-1, 110-2, 110-3 . . . which can display multiple measurement data points 116 or biomarkers 111 on information plots 112 which can also include a baseline 118 and/or a trend line 114 to help a user interpret results and detect possible trends in the data. The timeline 120 can be viewed using a time window 130 of a static or variable time duration 132, and a summary zoom window 134 can display summary information to assist in timeline navigation by a user.

One of the key features of the user interface for medical information 100 is that the timeline 120 can be highlighted or selected by the time window 130 with time duration 132, and the information plots 112 of biomarkers 111 displayed in the subsystem displays 110-1, 110-2, 110-3 . . . can update to display the biomarker information 111 for the time duration 132 highlighted by the time window 130. The trend line 114, baseline 118, and data points shown on the information plots 112 can also be adjusted to display only information during the time duration 132 highlighted or selected by the time window 130.

The timeline 120 functions to display the medical information collected over time, and can include icons for biological samples 122, icons for measurements 124, icons for sample indicators 126, icons for treatment indicators 128.

Biological samples 122 can include blood, urine, saliva, tissue, hair, nails, skin, bone fragments, biopsies, microbiome samples, stool samples, any combination thereof, or any other biological sample otherwise known in the art.

Biological Measurements 124 can one or more MR techniques, such as: magnetic-resonance imaging (MRI), magnetic-resonance spectroscopy (MRS), another MR technique, computed tomography, ultrasound imaging, X-ray imaging, positron emission spectroscopy, electron spin resonance, optical/infrared spectroscopy (e.g., to determine a complex index of refraction at one or more wavelengths), an electrical measurement (such as an electrocardiogram, an electromyogram, an electroencephalogram, etc.), proton beam, photoacoustic imaging, other non-destructive measurements (such as radar or millimeter-wave scanning), activity or behavior data for a biological organism (such as data capture using a wearable electronic device), measurements performed by nano particles in the biological sample, chemical composition of fluids (such as blood) measured at arbitrary locations in the biological organism non-destructively or by drawing a blood sample (e.g., using microfluidics), height, weight, a vital sign (pulse, respiration, temperature, blood pressure, etc.), genetic or genomic information (such as sequencing, next-generation sequencing, RNA sequencing, epigenetic information, etc.), quantitative tensor field maps, medical images, blood or lab tests, microbiome analysis, urine analysis, stool analysis, thermal-imaging readings, optical images, body impedance, biopsies, another quantitative or qualitative characteristic or property of the biological sample, etc.

Moreover, the MR technique may include quantitative analysis of MR scans such as MR fingerprints of the biological sample that are magnetic-field invariant (which are sometimes referred to as 'magnetic-field-invariant MR signatures' or 'invariant MR signatures'). The invariant MR signatures may describe the dynamic MR responses of voxels at 3D positions in the one or more biological samples at arbitrary magnetic-field strengths. Moreover, the invariant MR signatures may be independent of the MR scanners, as well as the specific scanning instructions (e.g., magnetic-field strengths and/or pulse sequences), used to acquire MR signals in a variation on MRF (which is sometimes referred to as 'quantitative MRF' or QMR-X) that were then used to determine the invariant MR signatures. An invariant MR signature may be determined by iteratively converging MR signals of one or more types of nuclei in the biological sample, which were acquired by an MR scanner based on scanning instructions, with simulated MR signals (which are sometimes referred to as calculated MR signals or estimated MR signals) for the biological sample that are generated using an MR model and the scanning instructions.

Furthermore, the MR technique may include: MRI, MRS, magnetic-resonance spectral imaging (MRSI), magnetic-resonance thermometry (MRT), magnetic-resonance elastography (MRE), MR fingerprinting (MRF), magnetic-field relaxometry, diffusion-tensor imaging and/or another MR technique (such as functional MRI, metabolic imaging, molecular imaging, blood-flow imaging, etc.). Note that these MR techniques are each a form of quantitative tensor-field mapping.

In particular, 'MRI' should be understood to include generating images (such as 2D slices) or maps of internal structure in a sample (such as anatomical structure in a biological sample, e.g., a tissue sample or a patient) based on the dynamic response of a type of nuclear spin (such protons or the isotope $^1$H) in the presence of a magnetic field, such as a non-uniform or spatially varying external magnetic field (e.g., an external magnetic field with a well-defined spatial gradient). In addition, MRS should be understood to include determining chemical composition or morphology of a sample (such as a biological sample) based on the dynamic response of multiple types of nuclear spins (other than or in addition to $^1$H) in the presence of a magnetic field, such as a uniform external magnetic field.

Moreover, 'MRSI' should be understood to include generating images or maps of internal structure and/or chemical composition or morphology in a sample using MRS in the presence of a magnetic field, such as a non-uniform or spatially varying external magnetic field. For example, in MRSI the measured dynamic response of other nuclei in addition to $^1$H are often used to generate images of the chemical composition or the morphology of different types of tissue and the internal anatomy of the biological sample.

Furthermore, in contrast with existing approaches to MRI or MRSI that usually provide qualitative or 'weighted' measurements of a limited set of properties, 'MRF' should be understood to include quantitative measurements of the properties of a sample by acquiring signals representing a dynamic or time-dependent magnetization or MR trajectory (such as in k-space) from different materials in a sample using a pseudorandom pulse sequence. In particular, instead of using repeated, serial acquisition of data to characterize individual parameters that are of interest, in MRF signals from different materials or tissues are often acquired using a pseudorandom pulse sequence to determine a unique signal or 'fingerprint' (e.g., a time-dependent magnetization or MR trajectory). The resulting unique fingerprint of the sample is, in general, a function of multiple material properties under investigation. For example, MRF can provide high-quality quantitative maps of: a spin-lattice relaxation time $T_1$ (which is the time constant associated with the loss of signal intensity as components of the nuclear-spin magnetization vector relax to be parallel with the direction of an external magnetic field), a spin-spin relaxation time $T_2$ (which is the time constant associated with broadening of the signal during relaxation of components of the nuclear-spin magnetization vector perpendicular to the direction of the external magnetic field), proton density (and, more generally, the densities of one or more type of nuclei) and diffusion (such as components in a diffusion tensor).

Note that 'magnetic-field relaxometry' (such as $B_0$ relaxometry with the addition of a magnetic-field sweep) may involve acquiring MR images at different magnetic-field strengths. These measurements may be performed on the fly or dynamically (as opposed to performing measurements at a particular magnetic-field strength and subsequently cycling back to a nominal magnetic-field strength during readout, i.e., a quasi-static magnetic-field strength). For example, the measurements may be performed using untuned radio-frequency (RF) coils or a magnetometer so that measurements at the different magnetic-field strengths can be performed in significantly less time.

Additionally, 'MRE' should be understood to include measuring the stiffness of a sample using MRI by sending mechanical waves (such as sheer waves) through a sample, acquiring images of the propagation of the shear waves, and processing the images of the shear waves to produce a quantitative mapping of the sample stiffness (which are sometimes referred to as 'elastograms') and/or mechanical properties (such as rigidity, density, tensile strength, etc.).

Moreover, 'MRT' should be understood to include measuring maps of temperature change in a sample using MRI.

The human icon 125 can represent a human form, but the icon could be of another species, or of a partial human form or other life form. The human icon functions to indicate an approximate location or related information for a biological sample 122, a measurement 124. This can improve the speed with which either a person or a medical practitioner or a technician or any other user can locate a specific sample on a timeline, e.g. if a user knows what they are looking for, the icon, when annotated with the appropriate biological samples 122 or measurements 124 can function as a shorthand to enable the user to find it faster.

The sample indicator 126 functions to indicate an amount of measurement and/or diagnostic activity, such as samples of tissue, tests of biomarkers, spatiotemporal measurements, thermal measurements, photography, imaging, quantitative measurements or any other suitable measurement or diagnostic activity. This can improve the comprehension of a reviewer or a medical practitioner or other user to understand the frequency with which samples were collected from a subject, and how comprehensively the testing and/or analysis that occurred. Regularly spaced sampling can correspond to a frequency of measurements such as regular checkup, while clusters can correspond to testing in response to at least one symptom or test result.

The treatment indicator 128 functions to indicate a therapy was applied to a biological life form and can further indicate the quantity of therapies and interventions that are being applied. The therapy can be applied when a medical practitioner prescribes it, when a subject starts self-medicating and self-reports, when a system reminds a user to take a medication for a chronic condition, etc. When combined with sample indicators 126 and/or displayed on the same timeline and/or in parallel with the same timeline, a reviewer or a medical practitioner or other user can draw a conclusion that a treatment was applied in response to a diagnosis from a sample indicated by a sample indicator 126, or a symptom or other input, including manual input from a medical practitioner, or self-medication from a subject themselves.

For both treatment indicators 128 and sample indicators 126, other alternative weighting schemes for displaying information known to practitioners of the art can be used to weight the displays of samples 126 and treatments 128 without affecting the function of giving a medical practitioner a high-level overview or "gestalt" perspective of the sampling and treatment history and the overall frequency of interactions with the healthcare system. Additionally, icons and color schemes can also be used to further communicate the information to a medical practitioner (e.g. green for samples or measurements captured, and red for interventions or treatments or therapies applied) such that patterns that can be easily detected by humans, such as regular and/or frequent interventions on the same part of the body or biological subsystem, or lack of access to a healthcare system will be readily apparent, and this can enhance the experience of the medical professional and enable them to make better diagnosis and treatment decisions on behalf of patients, as well as possibly reducing practitioner errors and saving practitioner time, which is a large expense.

The subsystem display 110, shown as 110-1, 110-2, 110-3, can focus on any number of biological subsystems in the human body, including Circulatory, Digestive, Renal/Urinary, Nervous, Endocrine, Reproductive, Integumentary, Musculoskeletal, Respiratory, Lymphatic, etc. The subsystem display can display a number of biomarkers or other measurement information 111 on an information plot 112.

The biomarkers 111 can have a non-anonymized identifier or an anonymized identifier, with the anonymized identifier being enabled for sensitive medical issues or information sharing between medical practitioners that can be regulated under HIPAA rules.

The information plot 112 functions to display information within a time window 130 defined by the time duration 132. As the time duration 132 is changed, or as the time window 130 is adjusted along time timeline, the information 111 and the display of the information 112 shown on the information plot can be adjusted to include or exclude information that now falls within the newly adjusted time window 130 or the newly adjusted time duration 132. In one embodiment, the time duration is static and is not adjustable. A zoom window 134 can provide summary information, thumbnail images, dates, references or other summary information to help a user navigate the timeline while looking for specific medical activity, including measurements, treatments, symptoms, etc.

Further, interpolation and extrapolation and visualization of the information plot 112 can include the actual data point 116. The interpolations and extrapolations can include a trend line 114, or a baseline 118. The trend line 114 functions to approximate the trend in the measurements, such as the measurement 116. A baseline 118 can be included for a flat level comparison, e.g. to help a human interpret or even detect a faint trend. The trend line 114 can be a straight line, or it can be a least squares, quadratic or cubic spline smoothed line or any other sort of interpolation or extrapolation technique. The interpolations and extrapolation computations for the trend line 114 can include information from samples outside of the time window 130 if required by the algorithm, or they can also exclude information from outside the time window 130.

Additionally, the ordering of multiple biomarkers or measurements 111 within the subsystem 110-1 can change as the time duration 132 or the time window 130 is adjusted. The ordering can be based on any number of factors or combinations thereof, including rankings of the most relevant biomarkers for understanding the health of that subsystem, rankings of biomarkers that have changed the most or the least since the previous measurement, biomarkers that are related to biomarkers that have changed the most since the most recent measurement, biomarkers that were flagged/labeled for follow up by a person's doctor in a previous visit, most recent capture, biggest change, relative volatility, relative stability, most significant risk (as determined by some sort of risk score, which can include or exclude a diagnostic risk score, and the risk score can be associated with each measurement or group of measurements).

Figure 2:
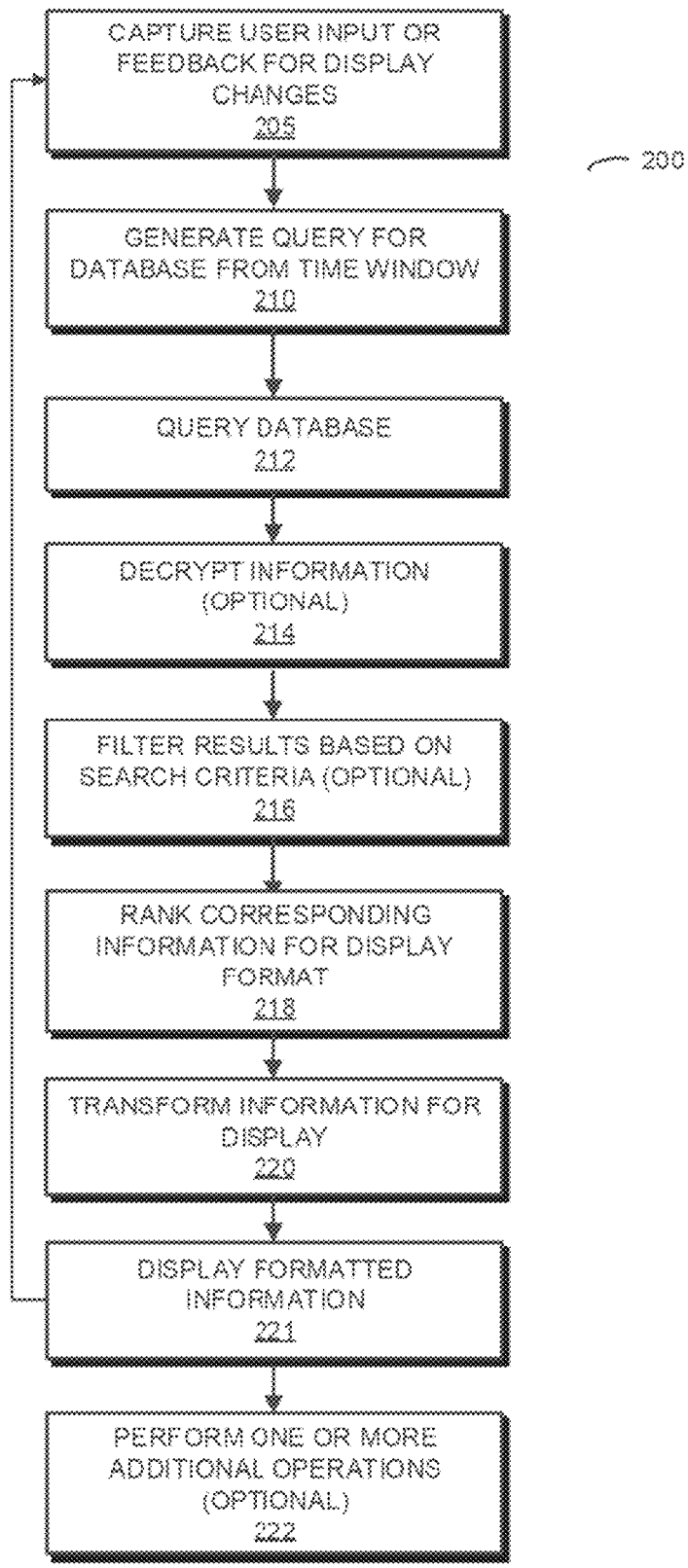
FIG. 2 is a block diagram illustrating a method of displaying medical information.

As shown in FIG. 2, a method 200 of displaying medical information includes capturing user input or feedback for display changes 205, generating the query for the database from a time window 210, querying the database 212, decrypting information 214, filter results based on search criteria 216, ranking corresponding information for display format 218, transforming information for display 220, and displaying formatted information 221.

Operation 205, capturing user input or feedback for display changes, captures user interactions with the display and can include capturing drag and drop prioritizations, reading in text entered into a text entry box, capturing voice input, capturing a selection area on a timeline or a drag of a fixed width or variable width window along a timeline, selection of a smoothing algorithm, selection of a specific data point, or any other suitable user input. The user input could be entered through a mouse, a keyboard, and a touch screen interface, voice spoken into a microphone and translated into commands. As the time duration (e.g. width of window) is changed, or as the time window is adjusted along time timeline to capture the same duration, but with a different start and end time, so will the captured input values for the time window.

Operation 210, generating the query for the database from a time window, functions to capture at least one start time and/or end time for a time window with which to query the database. The time window can be manually entered into a display, or it can be selected using a touch interface or a mouse. The time window is used to select a subset of information within the time duration. As the time duration (e.g. width of window) is changed, or as the time window is adjusted along time timeline to capture the same duration, but with a different start and end time, the generated query will change.

Figure 5:
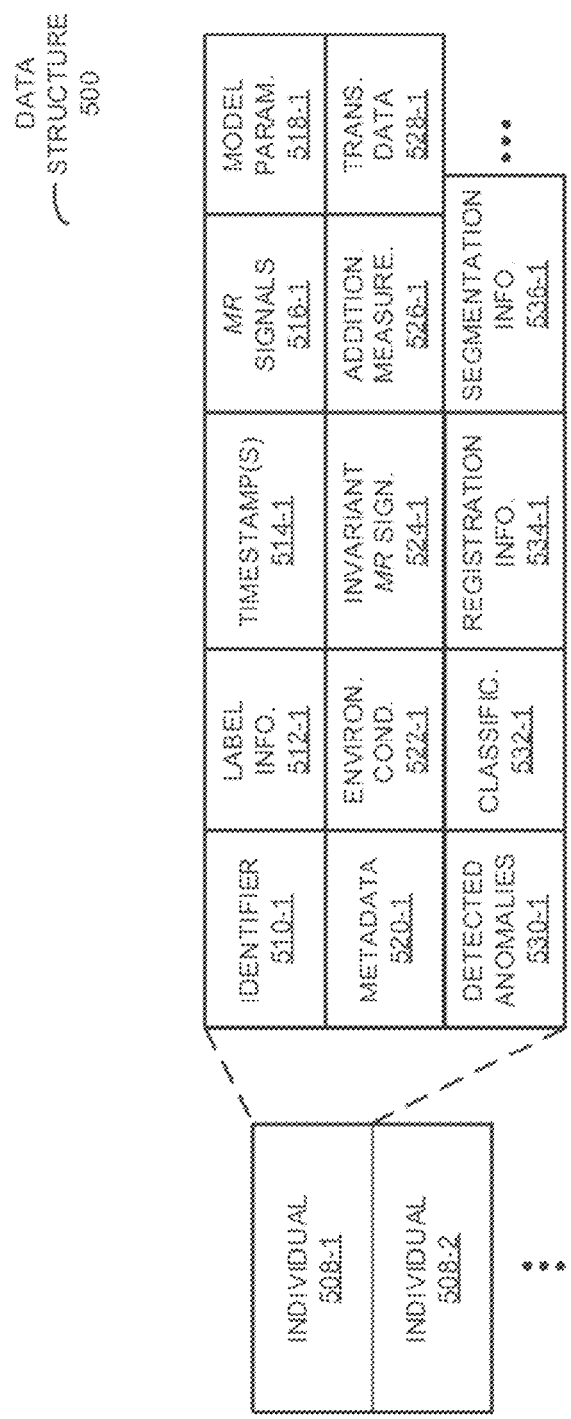
FIG. 5 is a drawing illustrating a data structure that is used by the electronic device of FIG. 4 in accordance with an embodiment of the present disclosure.

Operation 212, querying the database, sends a search query including the time window from operation 210 to a database. The database can be a distributed database, a NOSQL database, or any other suitable database. The database can include rows of information structured as shown in FIG. 5, which presents a drawing illustrating an example of a data structure 500. This data structure may include: an identifier 510-1 of individual 508-1, label information 512 (such as age, gender, biopsy results and diagnosis if one has already been made and/or any other suitable sample information, such as type of sample, which can include blood, saliva, hair, sweat, urine, tears, mucus, stomach acid, stool, cerebral spinal fluid CSF, tissue samples, etc.), timestamps 514 when data was acquired, received MR signals 516 (and, more generally, raw data), MR capture and model parameters 518 (including the voxel size, speed, resonant frequency, T1 and T2 relaxation times, signal processing techniques, RF pulse techniques, magnetic gradient strengths, the variable magnetic field B0, the pulse sequence, etc.), metadata 520 (such as information characterizing individual 508-1, demographic information, family history, optional segmentation data, data generated from or in response to the raw data, etc.), environmental conditions 522 (such as the temperature, humidity and/or barometric pressure in the room or the chamber in which individual 508-1 was measured), a determined invariant MR signature 524, one or more additional measurements 526 of physical properties of individual 508-1 (such as weight, dimensions, images, etc.), transformed data 528 generated from or in response to MR signals 516 (such as an estimated invariant MR signature), optional detected anomalies 530 (which, for a particular voxel, may include information specifying one or more of detected anomalies 530), optional classifications 532 of detected anomalies 530), registration information 534 and/or segmentation information 536. Note that data structure 500 may include multiple entries for test results over time, including genetic testing, cell free DNA/RNA, epigenetic testing, transcriotomic testing, proteomic testing, lipidomic testing, metabolomic testing, microbiomic testing. In one embodiment, data in data structure 500 is encrypted using a blockchain or a similar cryptographic hash technique to detect unauthorized modification or corruption of records. Moreover, the data can be anonymized prior to storage so that the identity of an individual is anonymous unless the individual gives permission or authorization to access or release the individual's identity.

Operation 214, decrypting information is an optional step, and can decrypt information retrieved in the query. This can also include requesting a password or authentication from a patient, a doctor or other medical practitioner or an artificial intelligence-based decision system. The medical information can require multiple encryption keys, such that the information can be decrypted when a patient/user and/or a medical practitioner both are present with decryption keys and/or other authentication information, such as GPS information for both the patient and the medical practitioner citing that they are both in approximately the same area. In many jurisdictions around the world it is recommended by law to encrypt medical information for security purposes. Note that the stored information may be encrypted, and also the returned query may be encrypted for transmission over a network. For example, symmetric or asymmetric encryption based on an encryption key associated with a unique identifier associated with a patient, a medical practitioner, or a medical record may be used.

Operation 216 filter results based on search criteria, filters the received results by search criteria received from a user or some automated criteria provided by an artificial intelligence-based decision system. An example of filtering the results would be filtering for a type of result (e.g. bio fluid tests, like blood and urine tests), or results within a specific time window, tests performed by a certain practitioner, or tests related to a specific disease or condition that might provide more insight to a medical practitioner or an artificial intelligence agent connected to the system. The filtered results can be filtered by biological subsystem, which can include any biological subsystem in the human body, including Circulatory, Digestive, Renal/Urinary, Nervous, Endocrine, Reproductive, Integumentary, Musculoskeletal, Respiratory, Lymphatic. The filter can select any number of biomarkers or other measurement information that will be prepared for display.

Operation 218, ranking corresponding information for display format, functions to rank or order the information for the display format. The ranking and/or ordering can be based on any number of factors or combinations thereof, including rankings of the most relevant biomarkers for understanding the health of that subsystem, rankings of biomarkers that have changed the most or the least since the previous measurement, biomarkers that are related to biomarkers that have changed the most since the most recent measurement, biomarkers that were flagged/labeled for follow up by a person's doctor in a previous visit, most recent capture, biggest change, relative volatility, relative stability, most significant risk (as determined by some sort of risk score, which can include or exclude a diagnostic risk score, and the risk score can be associated with each measurement or group of measurements).

Operation 220, transforming information for display functions to make the information more understandable to a human or machine interacting with the information. The transformations of the information can include interpolation and extrapolation and visualization of the information and can include overlays or underlays of the actual data points. The interpolations and extrapolations can include a trend line or a baseline. The trend line functions to approximate the trend in the measurements. A baseline can be included for a flat level comparison, e.g. to help a human interpret or even detect a faint trend. The trend line can be a straight line, or it can be a least squares, quadratic or cubic spline smoothed line or any other sort of interpolation or extrapolation technique. The interpolations and extrapolation computations for the trend line can include information from samples outside of the time window generated in Operation 205 if required by the algorithm, or they can also exclude information from outside the time window.

Operation 221 Displaying formatted information; functions to display the formatted information on a display. This display can be in a web browser on a computer or laptop, a mobile computing device, in a software application on a mobile device, on a TV channel or on a live stream over the Internet (for example, to medical students or other medical researchers on a collaborative team), or any other suitable display. This step can include generating on the fly arrangements for mobile screens.

Figure 4:
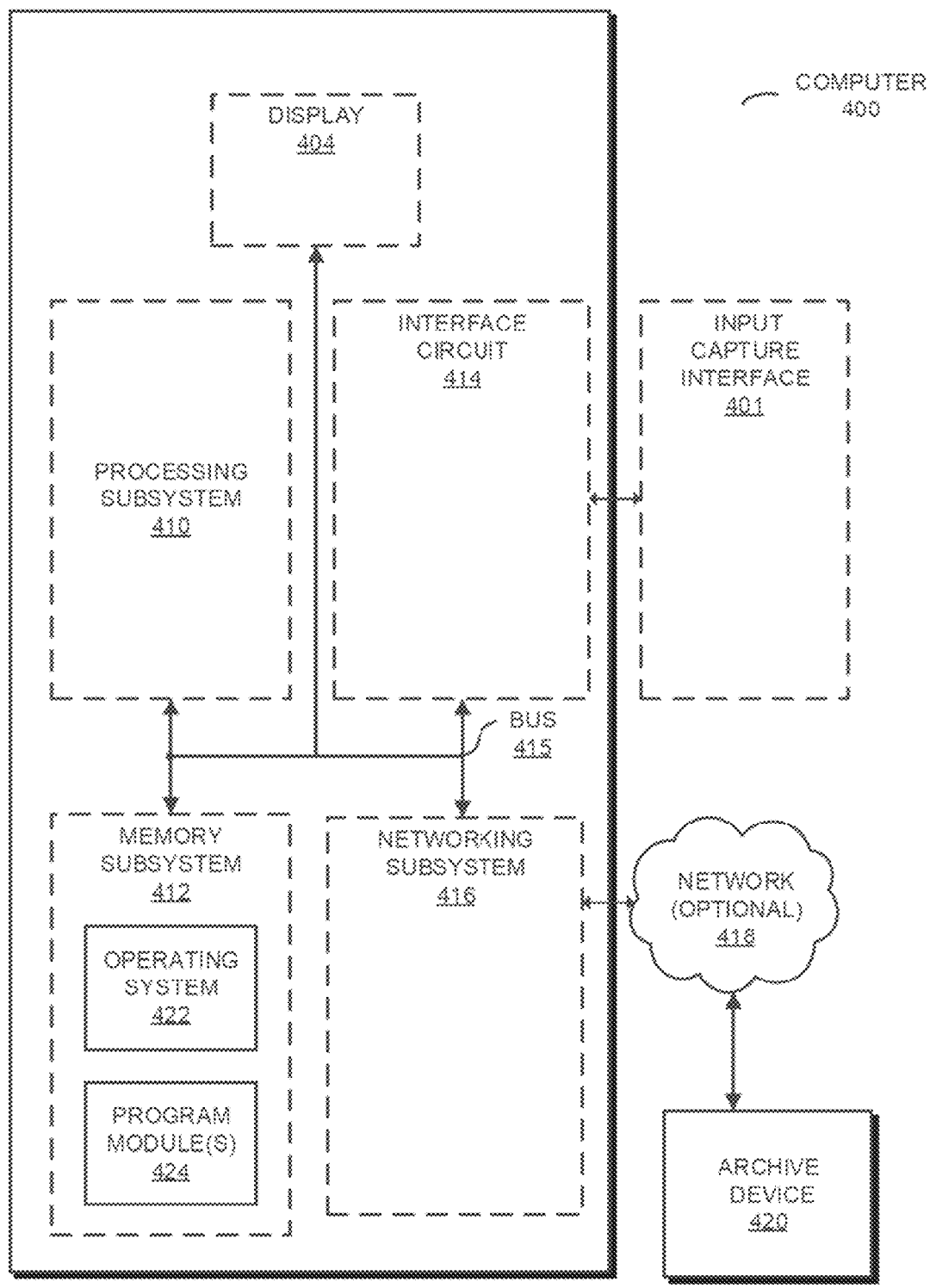
FIG. 4 is a block diagram illustrating a computer in the system of FIG. 3 in accordance with an embodiment of the present disclosure.

As shown in FIG. 4, the personal computing device or computer 400 includes processing subsystem 410 (and, more generally, an integrated circuit or a control mechanism), an input capture interface 401, a display 404, memory subsystem 412, and an interface circuit 414. Processing subsystem 410 includes one or more devices configured to perform computational operations and to execute techniques to process search queries input through the search capture interface 401 through the interface circuit. For example, processing subsystem 410 can include one or more microprocessors, graphical processing units (GPUs) application-specific integrated circuits (ASICs), microcontrollers, programmable-logic devices, and/or one or more digital signal processors (DSPs).

Memory subsystem 412 includes one or more devices for storing data and/or instructions for processing subsystem 410, interface circuit 414. For example, memory subsystem 412 can include dynamic random access memory (DRAM), static random access memory (SRAM), and/or other types of memory. In some embodiments, instructions for processing subsystem 410 in memory subsystem 412 include one or more program modules 424 or sets of instructions, which may be executed in an operating environment (such as operating system 422) by processing subsystem 410. Note that the one or more computer programs may constitute a computer-program mechanism or a program module. Moreover, instructions in the various modules in memory subsystem 412 may be implemented in: a high-level procedural language, an object-oriented programming language, and/or in an assembly or machine language. Furthermore, the programming language may be compiled or interpreted, e.g., configurable or configured (which may be used interchangeably in this discussion), to be executed by processing subsystem 410.

In addition, memory subsystem 412 can include mechanisms for controlling access to the memory. In some embodiments, memory subsystem 412 includes a memory hierarchy that comprises one or more caches coupled to a memory in the computer 400. In some of these embodiments, one or more of the caches is located in processing subsystem 410.

In some embodiments, memory subsystem 412 is coupled to one or more high-capacity mass-storage devices (not shown). For example, memory subsystem 412 can be coupled to a magnetic or optical drive, a solid-state drive, or another type of mass-storage device. In these embodiments, memory subsystem 412 can be used by the computer 400 as fast-access storage for often-used data, while the mass-storage device is used to store less frequently used data.

In some embodiments, memory subsystem 412 and processing subsystem 410 are coupled, via a network subsystem 416, possibly through a network 418, to an archive device 420. The archive device 420 can be a high-capacity network attached mass-storage device such as a network attached storage (NAS), an external hard drive, or a storage server, a cluster of servers, a cloud storage provider, a cloud computing provider, a magnetic tape backup system, a medical records archive service, or any other suitable archive devices. Moreover, in some embodiments, the processing subsystem 410 can interact with the archive device 420 using an Application Programming Interface (API) to store and/or request information from the archive device 420.

An example of the data stored (locally and/or remotely) in memory subsystem 412 or on archive device 420 is shown in FIG. 5, which presents a drawing illustrating an example of a data structure 500 that is used by electronic device 400 (FIG. 4). This data structure may include: an identifier 510-1 of individual 508-1, label information 512 (such as age, gender, biopsy results and diagnosis if one has already been made and/or any other suitable sample information, such as type of sample, which can include blood, saliva, hair, sweat, urine, tears, mucus, stomach acid, stool, cerebral spinal fluid CSF, tissue samples, etc.), timestamps 514 when data was acquired, received MR signals 516 (and, more generally, raw data), MR capture and model parameters 518 (including the voxel size, speed, resonant frequency, T1 and T2 relaxation times, signal processing techniques, RF pulse techniques, magnetic gradient strengths, the variable magnetic field B0, the pulse sequence, etc.), metadata 520 (such as information characterizing individual 508-1, demographic information, family history, optional segmentation data, data generated from or in response to the raw data, etc.), environmental conditions 522 (such as the temperature, humidity and/or barometric pressure in the room or the chamber in which individual 508-1 was measured), a determined invariant MR signature 524, one or more additional measurements 526 of physical properties of individual 508-1 (such as weight, dimensions, images, etc.), transformed data 528 generated from or in response to MR signals 516 (such as an estimated invariant MR signature), optional detected anomalies 530 (which, for a particular voxel, may include information specifying one or more of detected anomalies 530), optional classifications 532 of detected anomalies 530), registration information 534 and/or segmentation information 536. Note that data structure 500 may include multiple entries for test results over time, including genetic testing, cell free DNA/RNA, epigenetic testing, transcriotomic testing, proteomic testing, lipidomic testing, metabolomic testing, microbiomic testing. In one embodiment, data in data structure 500 is encrypted using a blockchain or a similar cryptographic hash technique to detect unauthorized modification or corruption of records. Moreover, the data can be anonymized prior to storage so that the identity of an individual is anonymous unless the individual gives permission or authorization to access or release the individual's identity.

The input capture interface 401 can capture user input or feedback for display changes or can also capture user interactions with the display and can include capturing drag and drop prioritizations, reading in text entered into a text entry box, capturing voice input, capturing a selection area on a timeline or a drag of a fixed width or variable width window along a timeline, selection of a smoothing algorithm, selection of a specific data point, or any other suitable user input. The user input could be entered through a mouse, a keyboard, and a touch screen interface, voice spoken into a microphone and translated into commands. As the time duration (e.g. width of window) is changed, or as the time window is adjusted along time timeline to capture the same duration, but possibly with a different start and end time, so will the captured input values for the time window.

The display 404, can be a screen for a personal computing device such as a desktop computer, a laptop computer, a personal computer, a workstation, a tablet, mobile phone, iPod touch, or other suitable personal computing device. The display could also be an optical projector, a laser projector, a television monitor, a hologram, or any other suitable display for displaying 2-dimensional or 3-dimensional images. The display 404 can be coupled to the processing subsystem 410 via a bus 415 and can receive image information of medical images of a subject, both before and after image processing performed by the processing subsystem 410 using program modules 424.

Networking subsystem 416 includes one or more devices configured to couple to and communicate on a wired, optical and/or wireless network (i.e., to perform network operations and, more generally, communication), For example, networking subsystem 416 may include: a Bluetooth™ networking system (which can include Bluetooth™ Low Energy, BLE or Bluetooth™ LE), a cellular networking system (e.g., a 3G/4G network such as UMTS, LTE, etc.), a USB networking system, a networking system based on the standards described in IEEE 802.11 (e.g., a Wi-Fi® networking system), or an Ethernet networking system.

Moreover, networking subsystem 416 includes processors, controllers, radios/antennas, sockets/plugs, and/or other devices used for coupling to, communicating on, and handling data and events for each supported networking or communication system. Note that mechanisms used for coupling to, communicating on, and handling data and events on the network for each network system are sometimes collectively referred to as a 'network interface' for the network system. Moreover, in some embodiments a 'network' between the electronic devices does not yet exist.

Within computer 400, processing subsystem 410, memory subsystem 412, interface circuit 414, networking subsystem 416 may be coupled using one or more interconnects, such as bus 415. These interconnects may include an electrical, optical, and/or electro-optical connection that the subsystems can use to communicate commands and data among one another. Note that different embodiments can include a different number or configuration of electrical, optical, and/or electro-optical connections among the subsystems.

Computer 400 can be (or can be included in) a wide variety of electronic devices. For example, computer 400 can be (or can be included in): a tablet computer, a smartphone, a portable computing device, test equipment, a digital signal processor, a cluster of computing devices, or any computing device (such as a laptop computer, a desktop computer, a server, and/or a subnotebook/netbook).

Although specific components are used to describe computer 400, in alternative embodiments, different components and/or subsystems may be present in the computer 400. For example, computer 400 may include one or more additional processing subsystems, memory subsystems, networking subsystems, and sensor subsystems. Additionally, one or more of the subsystems may not be present in computer 400.

Figure 3:
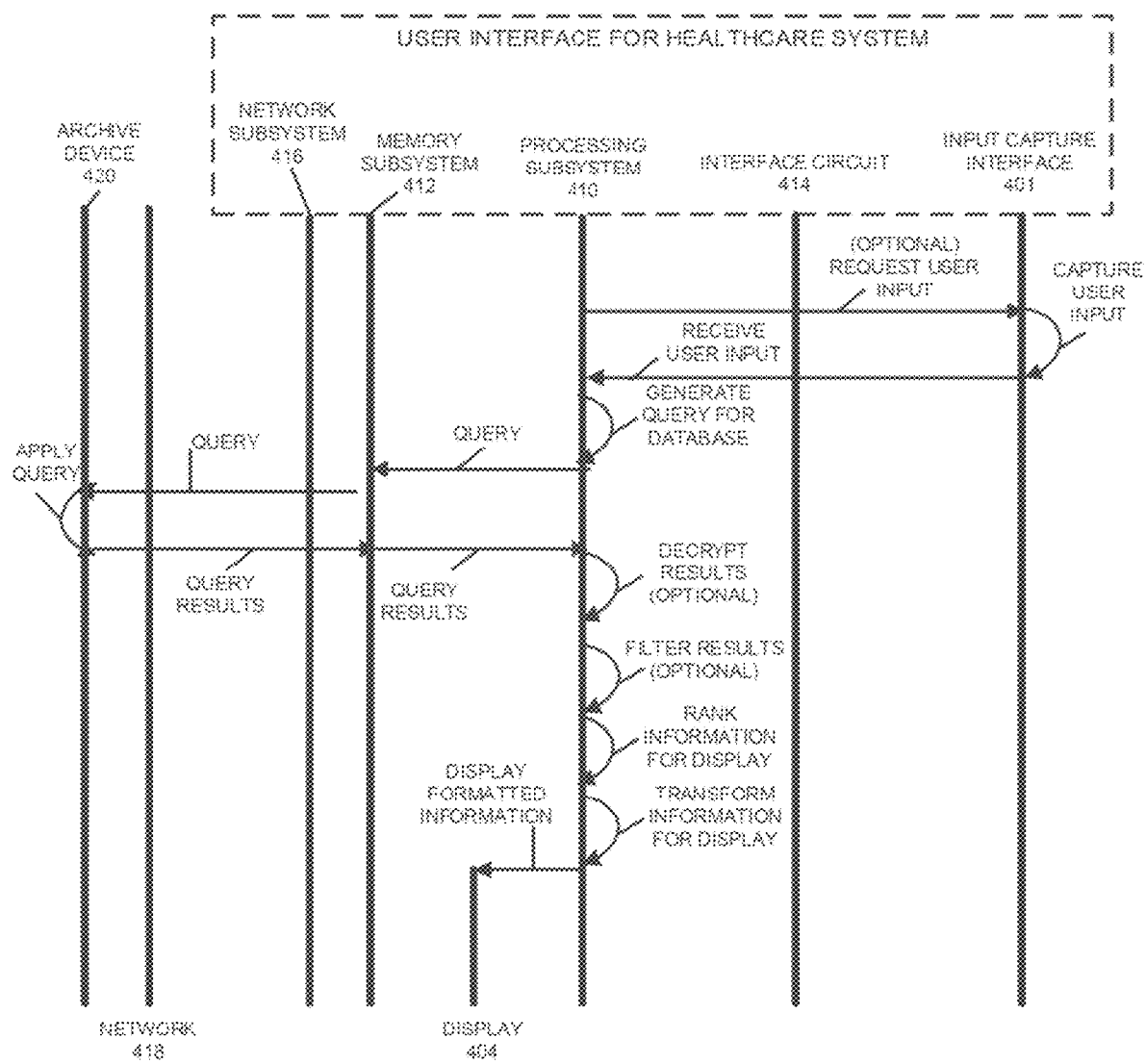
FIG. 3 is a drawing illustrating communication among components of a system during the method of FIG. 2 in accordance with an embodiment of the present disclosure.

Moreover, in some embodiments, computer 400 may include one or more additional subsystems that are not shown in FIGS. 3 and 4.

Although separate subsystems are shown in FIG. 4, in some embodiments, some or all of a given subsystem or component can be integrated into one or more of the other subsystems or components in a computer 400. For example, in some embodiments the one or more program modules 424 are included in operating system 422. In some embodiments, a component in a given subsystem is included in a different subsystem.

Moreover, the circuits and components in computer 400 may be implemented using any combination of analog and/or digital circuitry, including: bipolar, PMOS and/or NMOS gates or transistors. Furthermore, signals in these embodiments may include digital signals that have approximately discrete values and/or analog signals that have continuous values. Additionally, components and circuits may be single-ended or differential, and power supplies may be unipolar or bipolar.

An integrated circuit may implement some or all of the functionality of networking subsystem 416 (such as a radio) and, more generally, some or all of the functionality of computer 400. Moreover, the integrated circuit may include hardware and/or software mechanisms that are used for transmitting wireless signals from computer 400 to, and receiving signals at computer 400 from, other electronic devices. Aside from the mechanisms herein described, radios are generally known in the art and hence are not described in detail. In general, networking subsystem 416 and/or the integrated circuit can include any number of radios. Note that the radios in multiple-radio embodiments function in a similar way to the radios described in single-radio embodiments.

We now further describe operation of the computer 400 and the interactions between the computer 400 and the input capture device 401, the archive device 410. FIG. 2 presents a flow diagram illustrating a method 200 for ordering tests on medical samples, which may be performed by a processor in the computer 400. For example, the processor may execute a program module that includes instructions for operations in method 200.

In one embodiment the user interface for a healthcare system can be instructions in a program module 424 running on an operating system 422 stored in the memory subsystem 412 and executed on the processing subsystem 410, for the example embodiment above including the processing subsystem 410 requesting user input via the interface circuit 414 adapted to the input capture interface 401, capturing the user input with the input capture interface 401 (operation 205), and communicating the user input from input capture interface device 401 through the interface circuit 414 to the processing subsystem 410. From the captured user input captured by the input capture interface 401, the processing subsystem can generate a query for the database on the archive device 420 (operation 210). The query can be generated by the processing subsystem 410, stored in memory subsystem 412, and the query can be transmitted to the archive device 420 over a network 418 via the network subsystem 416, and the network subsystem can communicate with the memory subsystem 412 and the processing subsystem 410 via a system bus 415 (operation 212). The query generated by the processing subsystem can from a portion of the user input captured, for example a new start and/or end time can be determined by the processing subsystem from a selection area on a timeline in the captured user input or a drag of a fixed width or variable width window along a timeline in the captured user input, and the new start and/or end times can be included in the query generated in the processing subsystem 410.

The query can be applied in the archive device 420 to return results over the network 418 through the network interface 416 over the bus to the memory subsystem 412, where the query results can be stored and/or aggregated until the processing subsystem 410 is ready to process the query results. The processing subsystem can decrypt the results (operation 214), and while this step is optional, in many jurisdictions around the world it is recommended by law to encrypt medical information for security purposes. Note that the stored information may be encrypted, and also the returned query may be encrypted for transmission over the network 418. For example, symmetric or asymmetric encryption based on an encryption key associated with a unique identifier associated with a patient, a medical practitioner, or a medical record may be used.

The processing subsystem 410 can then filter results from one or more queries stored in the memory subsystem 412 (operation 216), also an optional step, as unfiltered results can be cached and saved in memory subsystem 412, for future queries and may be able to adjust the displayed information without sending a query over the network 418 to the archive device. This will depend on the amount of computer system resources and network bandwidth available to the computer 400, and the size of the query. An example of filtering the results would be filtering for a type of result (e.g. bio fluid tests, like blood and urine tests), or results within a specific time window, tests performed by a certain practitioner, or tests related to a specific disease or condition that might provide more insight to a medical practitioner or an artificial intelligence agent connected to the system.

The processing subsystem 410 can then rank the information for display (operation 218). The ranking can be according to a predefined standard ranking methodology (such as what users are most likely to be interested in viewing first), or it can be ranked by deviations from expected values, increases in rates of change of a measurement, medical practitioner inputs, or other methods of anomaly detection.

The processing subsystem 410 can also transform the information for display (operation 220), which can include filtering, adding moving averages, applying filtering techniques, volatility measurements and estimates, predictions, interpolations, visualizations, or any other suitable transformations to the data retrieved from the query. These transforms can be stored in the memory subsystem 412 and can also be stored in the archive device 420, if transmitted over the network 418. The transform can also include formatting the information for display, where such formatting can be in a markup language such as HTML or XML, or any other suitable formatting known to the art. An example of this formatting is displayed in FIG. 1.

The processing subsystem can then transmit the information to the display 404 (operation 221). The display 404 can be a monitor or other screen device that can simply display the formatted information transmitted to it over the bus 415 from the processing subsystem 410, or the display can have built in software that can provide additional processing and/or formatting.

In some embodiments of one or more of the preceding methods, there may be additional or fewer operations. Furthermore, the order of the operations may be changed, and/or two or more operations may be combined into a single operation. In addition, in some of the preceding embodiments there are fewer components, more components, a position of a component is changed, and/or two or more components are combined.

In the preceding description, we refer to 'some embodiments.' Note that 'some embodiments' describes a subset of all of the possible embodiments but does not always specify the same subset of embodiments.

The foregoing description is intended to enable any person skilled in the art to make and use the disclosure and is provided in the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Additionally, the discussion of the preceding embodiments is not intended to limit the present disclosure. Thus, the present disclosure is not intended to be limited to the embodiments shown but is to be accorded the widest scope consistent with the principles and features disclosed herein.

What is claimed is:

1. A computer-implemented method for displaying and analyzing medical information, the method comprising:
generating a timeline configured to display a plurality of icons comprising instances of a lifeform icon and two or more of: a biological sample icon, a measurement icon, a sample indicator icon, a treatment indicator icon, and combinations thereof, wherein two or more instances of the biological sample icon, the measurement icon, the sample indicator icon and the treatment indicator icon are indicated at different timestamps along the timeline corresponding to when samples were acquired or treatments were performed, and wherein a given instances of the lifeform icon comprises a graphical representation of a human body and indicates an approximate location on the human body where one or more of a biological sample, a measurement, a sample and a combination thereof are associated or were acquired;
generating a sliding window on the timeline, wherein the sliding window highlights a subset of the plurality of icons, and wherein the sliding window has an adjustable width and location; and
displaying data points in information plots in a subsystem display, wherein the data points are related to the subset of the plurality of icons highlighted in the sliding window, and
wherein the information plots correspond to different organ subsystems in a lifeform and a given information plot comprises a name of a given organ subsystem and the data points corresponding to the two or more of the biological sample icon, the measurement icon, the sample indicator icon and the treatment indicator icon that are associated with the given organ subsystem.

2. The computer-implemented method of claim 1, wherein the sample indicator icon is a representation of a quantity of the data points collected at a specific point in time.

3. The computer-implemented method of claim 1, wherein the data points are biomarkers.

4. The computer-implemented method of claim 3, further comprising ordering the data points based on one or more of: relevance, a degree of change relative to a previous data point, relatedness to other data points, a label, relative volatility, relative stability, health risk, deviations from expected values, increases in a rate of change of a data point, medical practitioner input, and combinations thereof.

5. The computer-implemented method of claim 1, further comprising receiving a user input to adjust one or more of a width and a location of the sliding window.

6. The computer-implemented method of claim 5, further comprising receiving a user input to zoom in on a subset of the plurality of icons.

7. The computer-implemented method of claim 5, wherein adjusting the sliding window captures one of: a same duration time window, a different duration time window, a different start time, a different end time, and combinations thereof.

8. The computer-implemented method of claim 5, further comprising updating the data points displayed in the subsystem display when the sliding window is adjusted.

9. The computer-implemented method of claim 1, further comprising displaying the treatment indicator icon on the given instances of the lifeform icon to represent an approximate location a treatment.

10. The computer-implemented method of claim 1, wherein the data points comprise one or more data points from outside the sliding window for interpolation.

11. The computer-implemented method of claim 1, further comprising decrypting the data points.

12. The computer-implemented method of claim 1, wherein the information plot corresponding to the given organ subsystem comprises one or both of a baseline and a trend line.

13. The computer-implemented method of claim 1, wherein the biological sample icon represents one or more of: a blood sample, a urine sample, a saliva sample, a hair sample, a nail sample, a skin sample, a bone fragment sample, a biopsy, a microbiome sample, a stool sample, and combinations thereof.

14. The computer-implemented method of claim 1, wherein the measurement icon represents one or more of: MR techniques, X-ray techniques, imaging techniques, vital signs, genetic information, sample analyses, and combinations thereof.

15. The computer-implemented method of claim 1, further comprising:
receiving search criteria from a user; and
automatically adjusting the sliding window based on the search criteria.

16. A non-transitory computer-readable storage medium for use in conjunction with a computer system, the computer-readable storage medium configured to store program instructions that, when executed by the computer system, causes the computer system to perform operations comprising:
generating a timeline configured to display a plurality of icons comprising instances of a lifeform icon and two or more of: a biological sample icon, a measurement icon, a sample indicator icon, a treatment indicator icon, and combinations thereof, wherein two or more instances of the biological sample icon, the measurement icon, the sample indicator icon and the treatment indicator icon are indicated at different timestamps along the timeline corresponding to when samples were acquired or treatments were performed, and wherein a given instances of the lifeform icon comprises a graphical representation of a human body and indicates an approximate location on the human body where one or more of a biological sample, a measurement, a sample and a combination thereof are associated or were acquired;
generating a sliding window on the timeline, wherein the sliding window highlights a subset of the plurality of icons, and wherein the sliding window has an adjustable width and location; and
displaying data points in information plots in a subsystem display, wherein the data points are related to the subset of the plurality of icons highlighted in the sliding window, and
wherein the information plots correspond to different organ subsystems in a lifeform and a given information plot comprises a name of a given organ subsystem and the data points corresponding to two or more of the biological sample icon, the measurement icon, the sample indicator icon and the treatment indicator icon that are associated with the given organ subsystem.

17. The computer program product of claim 16, wherein the operations further comprise transforming the data points, and wherein transforming comprises one or more of: filtering, adding moving averages, applying filtering techniques, applying volatility measurements, applying estimates, applying predictions, applying interpolations, applying visualizations, and combinations thereof.

18. A system for displaying and analyzing medical information, the system comprising:
a processor subsystem configured to execute program instructions;
a memory subsystem, coupled to the processor subsystem, configured to store the program instructions, wherein, when executed by the processor subsystem, the program instructions cause the system to perform operations comprising:
generating a timeline configured to display a plurality of icons comprising instances of a lifeform icon and two or more of: a biological sample icon, a measurement icon, a sample indicator icon, a treatment indicator icon, and combinations thereof, wherein two or more instances of the biological sample icon, the measurement icon, the sample indicator icon and the treatment indicator icon are indicated at different timestamps along the timeline corresponding to when samples were acquired or treatments were performed, and wherein a given instances of the lifeform icon comprises a graphical representation of a human body and indicates an approximate location on the human body where one or more of a biological sample, a measurement, a sample and a combination thereof are associated or were acquired;
generating a sliding window on the timeline, wherein the sliding window highlights a subset of the plurality of icons, and wherein the sliding window has an adjustable width and location; and
displaying data points in information plots in a subsystem display, wherein the data points are related to the subset of the plurality of icons highlighted in the sliding window, and
wherein the information plots correspond to different organ subsystems in a lifeform and a given information plot comprises a name of a given organ subsystem and the data points corresponding to the two or more of the biological sample icon, the measurement icon, the sample indicator icon and the treatment indicator icon that are associated with the given organ subsystem.

19. The system of claim 18, wherein the operations further comprise receiving user input via an input capture interface, and wherein the user input comprises one or more of: search criteria for automatically adjusting the sliding window, an adjustment of a width of the sliding window, an adjustment of a location of the sliding window, and combinations thereof.

20. The system of claim 19, wherein the operations further comprise communicating the user input from the input capture device through an interface circuit to the processing subsystem.

* * * * *